United States Patent [19]

Alexander

[11] 4,419,100

[45] Dec. 6, 1983

[54] OSTOMY APPLIANCE AND FACEPLATE ATTACHMENT THEREFOR

[75] Inventor: Brian S. Alexander, Evanston, Ill.

[73] Assignee: Hollister Incorporated, Libertyville, Ill.

[21] Appl. No.: 358,689

[22] Filed: Mar. 16, 1982

[51] Int. Cl.³ .............................................. A61F 5/44
[52] U.S. Cl. .................................. 604/339; 604/341
[58] Field of Search ............... 604/332, 336, 337, 338, 604/339, 341–345

[56] References Cited

U.S. PATENT DOCUMENTS

| | | | |
|---|---|---|---|
| 1,763,574 | 6/1930 | Williams. | |
| 1,821,274 | 9/1931 | Plummer. | |
| 2,366,059 | 12/1944 | Schunk | 604/334 |
| 2,684,676 | 7/1954 | Perry | 128/283 |
| 3,021,843 | 2/1962 | Perry | 604/339 |
| 3,123,074 | 3/1964 | Turner | 604/332 |
| 3,398,744 | 8/1968 | Hooper | 128/283 |
| 3,528,420 | 9/1970 | Nielsen | 604/342 |
| 3,618,606 | 11/1971 | Brown | 604/334 |
| 3,759,415 | 9/1973 | Cloyd | 220/60 |
| 3,817,420 | 6/1974 | Heisler | 220/60 R |
| 3,902,496 | 9/1975 | Eakin | 128/283 |
| 4,078,567 | 3/1978 | Fenton | 604/342 |
| 4,109,657 | 8/1978 | Carrington | 128/283 |
| 4,170,231 | 10/1979 | Collins | 128/283 |
| 4,213,458 | 7/1980 | Nolan | 128/283 |
| 4,232,672 | 11/1980 | Steer et al. | 128/283 |

FOREIGN PATENT DOCUMENTS

| | | |
|---|---|---|
| 2316142 | 1/1977 | France. |
| 118509 | 8/1969 | Sweden. |
| 799986 | 8/1958 | United Kingdom. |

*Primary Examiner*—C. Fred Rosenbaum
*Assistant Examiner*—J. L. Kruter
*Attorney, Agent, or Firm*—Tilton, Fallon, Lungmus

[57] ABSTRACT

An ostomy appliance in which a pair of semi-rigid coupling rings and a flexible, resilient web are utilized for detachably connecting a collection pouch to a flexible faceplate. The appliance consists of two main parts: a pouch on which one of the coupling rings is mounted, and a faceplate to which the other of the rings is connected by means of the flexible annular web. The web allows limited floating action between the second coupling ring and the faceplate.

17 Claims, 5 Drawing Figures

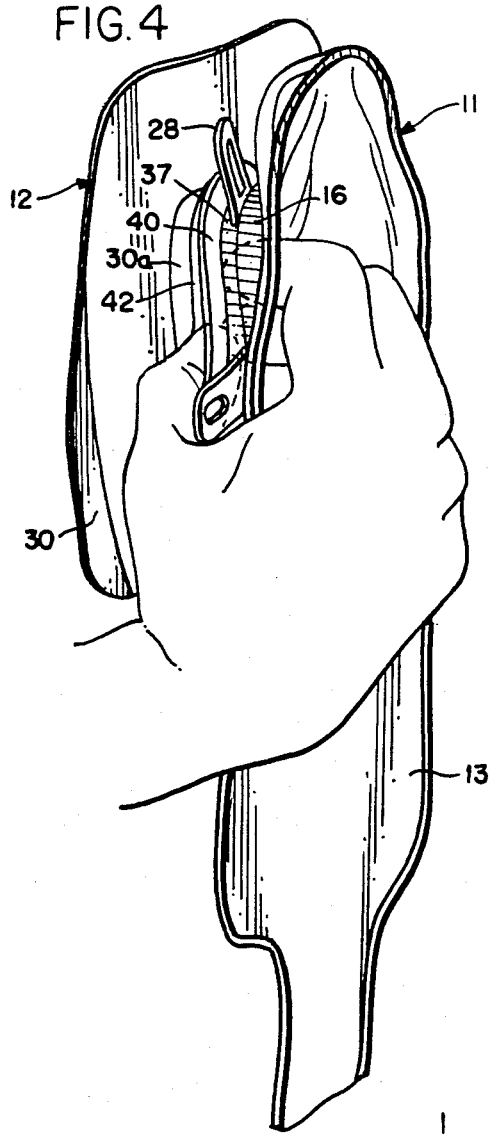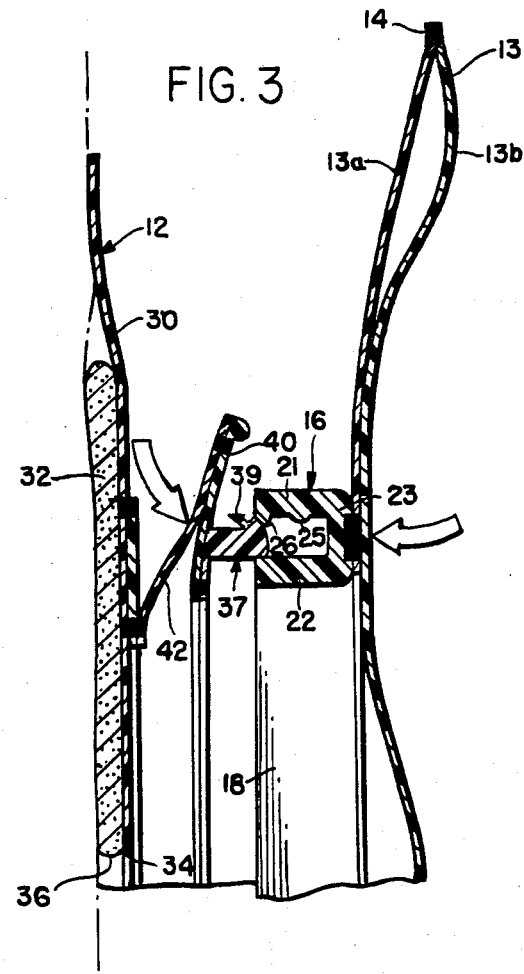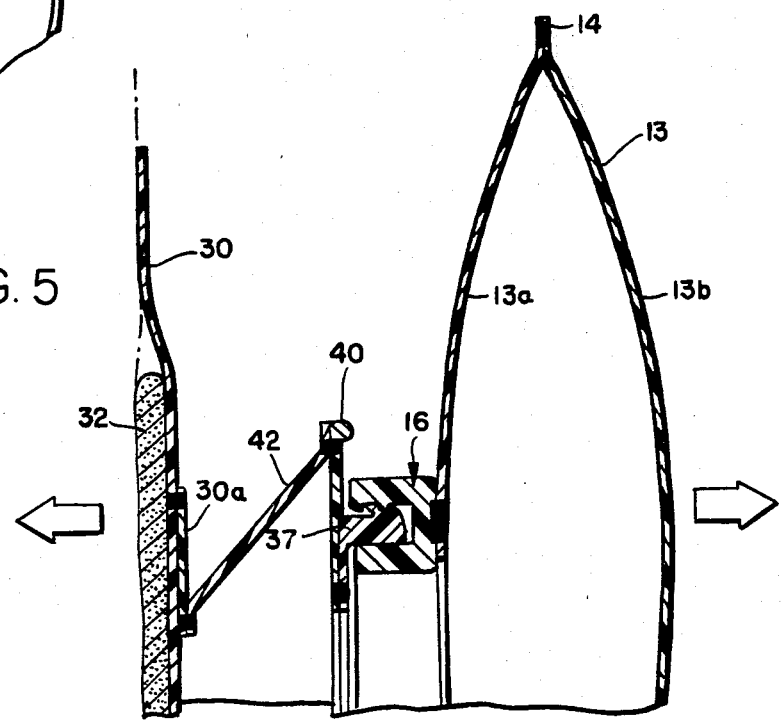

OSTOMY APPLIANCE AND FACEPLATE ATTACHMENT THEREFOR

BACKGROUND AND SUMMARY

For a number of years, ostomy appliances have been commercially available with plastic coupling rings that mate together in a manner similar to the rims of plastic food containers, photographic film containers, and the like. With one of the rings mounted upon the collection pouch and the other secured to a faceplate adhered to the wearer about the stoma opening, the wearer may couple and uncouple the rings for purposes of venting, draining, or replacing the pouch, or for any other reason, without breaking the adhesive seal between the faceplate and the wearer's skin. Detachability of the pouch is therefore achieved while at the same time providing a faceplate that may remain adhered to the wearer for an extended period that suits his/her comfort and convenience.

U.S. Pat. No. 4,232,672 discloses a pair of plastic coupling rings used in the manner described above. Like the mating rims of other types of containers or closures, one ring is provided with a channel, and the other ring has a deformable insert element receivable in that channel. U.S. Pat. No. 4,170,231 similarly illustrates an ostomy appliance having a pair of flexible plastic coupling rings for detachably supporting the pouch upon the faceplate. Other patents of interest are U.S. Pat. Nos. 3,817,420, 3,759,415, France Pat. No. 2,316,142, and Sweden Pat. No. 351,610.

Regardless of the details of construction, flexible plastic coupling rings used for ostomy appliances must be capable of providing a fluid-tight seal and must also provide an interlock that is tight enough to avoid unintentional detachment of the pouch from the faceplate. For such purposes, the mating thermoplastic rings must have wall thicknesses and/or compositions that provide the rings with sufficient stiffness to insure a secure coupling. Unfortunately, the advantages that such stiffness provide are offset by patient discomfort not only during the wearing of the appliance but also when coupling or uncoupling is desired. To secure the parts together, the pouch ring must be pushed into tight locking engagement with the faceplate ring, and the application of such force against the faceplate and the tender peristomal skin below it may cause considerable wearer discomfort. Removal presents a similar problem, since the pulling force needed to separate the rings may be transmitted to the faceplate to the peristomal area causing patient discomfort and, at least in some instances, causing the faceplate ring to pull way from the body, increasing the possibilities of subsequent leakage and/or reducing the wearing time for the appliance. If, in order to reduce discomfort associated with attaching the coupling rings, a patient uses only minimal force to couple such rings, there is a risk that the mechanical seal will be insufficient to prevent the leakage of odors, fluids, or solid materials, and may even be insufficient to retain the collection pouch in place.

Accordingly, it is a main object of this invention to provide an improved coupling which permits the wearer (or attendant) to attach and detach the coupling rings without the transmission of any appreciable pulling or pushing forces to the peristomal (or periwound) area. Since the discomforts associated with attachment and detachment are eliminated or at least greatly reduced, the chances that a user might incompletely join the coupling rings are also reduced.

Another important aspect of this invention lies in providing a secure but disconnectable coupling comprising a pair of semi-rigid coupling rings which, despite their stiffness, allow full conformity of the faceplate to the peristomal area, even when the wearer bends, turns, and moves about. Such a construction virtually eliminates the possibility that wearer movement might result in unintentional uncoupling of the plastic rings from each other. Since the coupled rings do not interfere with limited flexing and deforming of the faceplate, the construction of this invention may be used effectively with patients who, because of obesity or awkward stoma location, would be unable to wear current appliances with detachable plastic coupling rings. Distortions of the faceplate that would be resisted or prevented by the coupling rings of prior constructions are absorbed by the floating interconnection of this invention, thereby avoiding the transmission of stresses that might otherwise result in unintentional uncoupling of the rings, or a peeling away of the faceplate from the patient, or an incomplete attachment of the faceplate to the patient in the first instance.

Briefly, an ostomy appliance embodying this invention includes a pair of semi-rigid coupling rings detachably connectable to each other, one of the rings (referred to as the first ring) being secured to a flexible collection pouch so that the opening of the ring communicates with the pouch's interior, and the other (second) ring being mounted upon a highly flexible faceplate adapted to be adhesively secured to the peristomal surface of a wearer's body. The second coupling ring is mounted upon the faceplate by means of a flexible and resilient thermoplastic web. The web is annular in configuration, having an outer edge portion secured to the periphery of the second ring and an inner edge portion secured to the faceplate about the aperture thereof. Because the web is formed from a relatively thin, resilient, and deformable plastic film, it permits limited movement of the second ring in generally axial directions with respect to the faceplate, thereby facilitating attachment of the two coupling rings, or detachment of those rings, without the transmission of pushing or pulling forces to the faceplate and to the peristomal area to which it is secured. In addition, the flexible and resilient annular web permits conformity of the faceplate to a wearer's body without objectionable resistance from the relatively stiff coupling rings. The resilient web thereby provides a non-rigid interconnection between a pliable or deformable faceplate and the coupling ring assembly, allowing the ring assembly to float to a limited extent with respect to the faceplate, and vice versa.

In the embodiment disclosed, the second ring (i.e., the one mounted upon the faceplate) includes a radially and circumferentially extending annular flange portion having a bead extending about the outer perimeter thereof. Additionally, the flange may be provided with a slight but definite curvature (when viewed in radial section) with the convex surface of the flange facing towards the faceplate, so that when the parts are in untensioned or undistorted condition, the bead of the flange is normally spaced a slight distance from the faceplate. In either event, a user may easily and quickly insert his/her fingers between the flange and faceplate to brace the flange and the second coupling ring when the two coupling rings are to be latched together. Similarly, when the rings are to be disconnected, the second ring may be easily gripped by its enlarged flange portion and held in place while a tab-equipped portion of the first ring (the ring connected to the collection pouch) is pulled away.

The flexible and resilient annular web is secured to the beaded periphery of the second coupling rings's flange portion. Such web and other components are preferably formed of thermoplastic materials and heat-sealed to each other.

Other features, advantages, and objects of the invention will become apparent from the specification and drawings.

DRAWINGS

FIG. 3 is similar to FIG. 2 but illustrates the relationship of parts during a coupling operation.

FIG. 4 is a perspective view showing the parts as they might be oriented and held during a coupling operation.

FIG. 5 is a fragmentary sectional view similar to FIG. 3 but showing the coupling rings fully engaged and illustrating the range of floating movement afforded by the connecting web.

DETAILED DESCRIPTION

Figure 1:
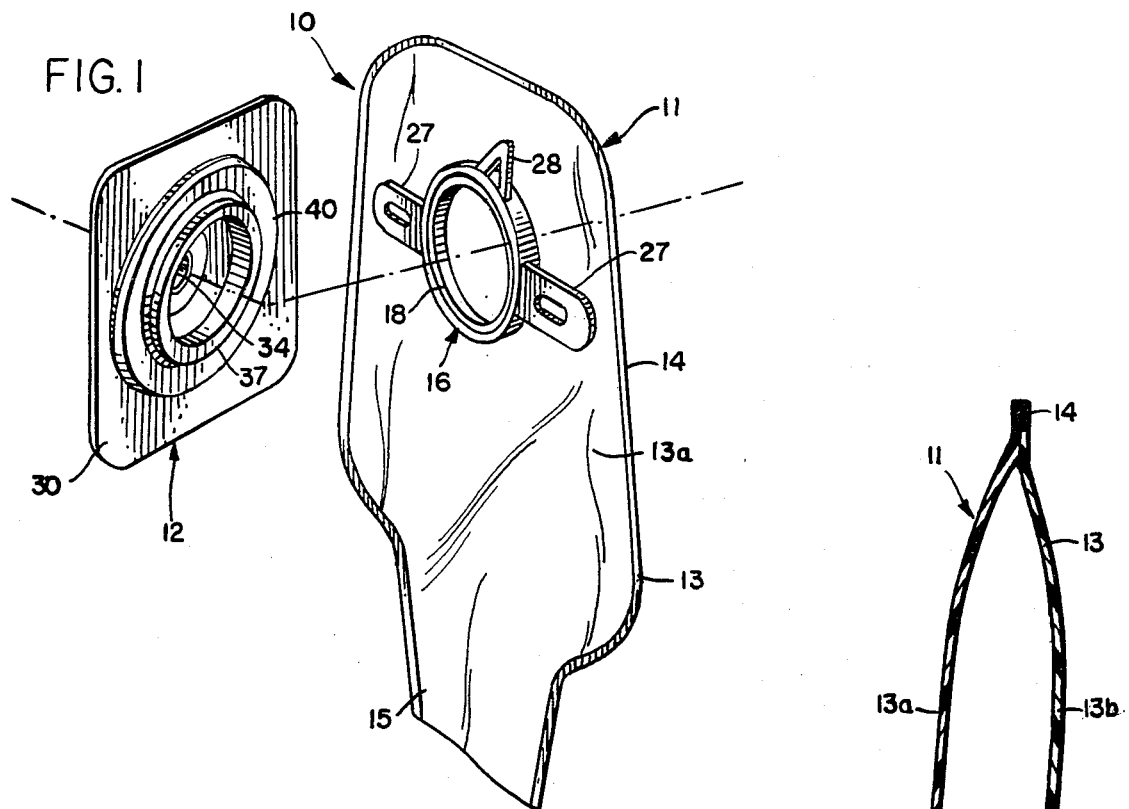
FIG. 1 is a perspective view of the two main components of the ostomy appliance, such components being depicted in detached condition.

FIG. 1 illustrates a two-part ostomy appliance 10 consisting of a pouch assembly 11 and a faceplate assembly 12. The pouch assembly includes a collection pouch 13 which may be formed of two panels 13a and 13b joined together by a peripheral zone of heat sealing 14 and terminating in an open neck portion 15 at the pouch's lower end. Where such a neck portion is provided, a suitable clamp, such as the clamp disclosed in U.S. Pat. No. 3,523,534, would be used to maintain the pouch's lower end in closed condition. Alternatively, neck portion 15 may be omitted entirely and the heat-sealing zone 14 may extend about the full periphery of the pouch.

A first coupling ring 16 is secured to one wall 13a of the pouch by heat sealing at 17 or by any other suitable means. The coupling ring 16 has a generally circular configuration, defining a central opening 18 which communicates with the interior 19 of the pouch through aperture 20 in the upper portion of panel 13a. When viewed in section, the coupling ring 16 is U-shaped, having spaced outer and inner walls 21 and 22 joined by an integral intermediate wall 23, the latter being secured by heat seal 17 to panel 13a of the pouch. The channel 24 of the coupling ring 16 therefore faces away from pouch 13 in a generally rearward direction with respect to the wearer. Within channel 24, a pair of latching ribs 25 and 26 are provided by outer wall 21. Referring to FIG. 1 a pair of apertured tongues 27 may project laterally from opposite sides of the coupling ring 16 for the attachment of a suitable support belt, if the use of such a belt is desired by the wearer. An integral tab 28 also projects radially outwardly from the periphery of coupling ring 16 to serve as a handle for pulling ring 16 away from the faceplate assembly 12 during an uncoupling operation.

In the embodiment illustrated, the faceplate assembly 12 includes a highly flexible faceplate 30 preferably formed of a gas-penetrable but water resistant microporous material. Various materials having such properties are known and may be used. For example, a reinforced non-woven cellulosic material of the type sold under the Kaycel trademark by Kimberly-Clark Corporation, Neenah, Wisconsin may be used. Such material is not only air-pervious but is surface-coated with an ethyl vinyl acetate latex emulsion so that it is also heat-sealable. A porous, expanded, high-density polyethylene or polypropylene film of the type marketed under the designation Delnet by Hercules Incorporated, Wilmington, Del. may be included for strength and soil resistance, and other porous thermoplastic films or membranes such as Gore-tex, a microporous polytetrafluoroethylene membrane marketed by W. L. Gore & Associates, Newark, Del., may also be employed. Effective results have been obtained utilizing copolymer films of ethylene and vinyl acetate laminated to non-woven polyester or non-woven rayon layers. In any case, the faceplate should be highly flexible, so that it will conform readily to body contours and body movements, and be relatively strong and durable. It should be coated on its back or rear side with a medical-grade pressure-sensitive adhesive so that upon removal of backing sheets 31 of the microporous faceplate may be adhesively secured to the patient's skin in the peristomal region.

Figure 2:
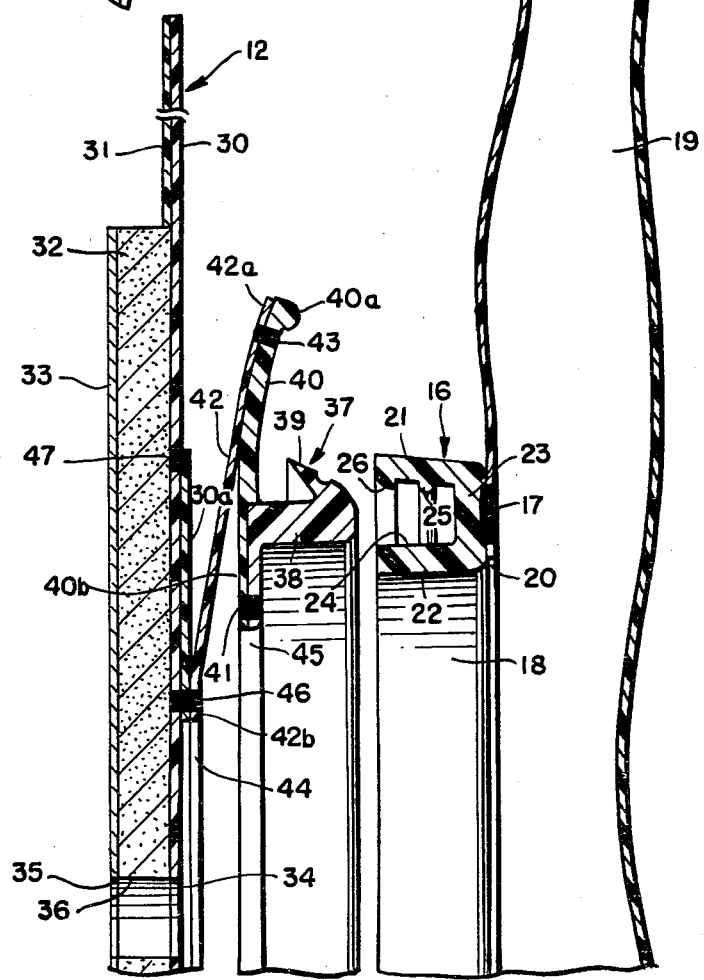
FIG. 2 is a somewhat schematic vertical sectional view showing the main components in separated and untensioned condition.

If desired, the backside of the faceplate may have a resilient sealing ring 32 secured thereto. The sealing ring may be formed of any pliable and tacky material capable of sealingly engaging the peristomal area to prevent the escape of liquids and gases. Since rings formed of karaya-glycerol mixtures and other materials are well known for such purposes, and since the ring is not an essential part of this invention and may, in fact, be omitted entirely, further discussion is believed unnecessary herein. Where provided, such a ring would have its rear surface covered by a removable release or backing sheet 33 as shown in FIG. 2. Otherwise, the release sheet 33 would be applied directly to the adhesive coating along the rear side of faceplate 30.

The faceplate 30 is generally rectangular in outline and is provided with a small central opening 34, as shown most clearly in FIG. 1. Backing 33 and sealing ring 32 (when provided) have openings 35 and 36 in register with opening 34 (FIG. 2). The aligned openings provide a starting point where a user may insert the blade of a pair of scissors to cut an opening in the faceplate (and in backing 31, 33 and, if provided, sealing ring 32) to form a larger opening that matches a patient's stoma.

A second coupling ring 37 is mounted upon faceplate 30 in the manner shown most clearly in FIGS. 2–4. In the particular embodiment illustrated, the second coupling ring includes an insert portion 38 adapted to be received within the channel 24 of the first coupling ring 16. The insert portion has an integral spring latching member 39 which is engagable with outer wall 21 of ring 16 to perform the dual functions of forming a fluid-tight seal between the parts and of establishing a double-latch that locks the two rings against unintentional disconnection (FIG. 5). The second coupling ring 37 also includes a radially- and circumferentially-extending annular flange portion 40. In the illustration given, flange portion 40 and insert portion 38 are formed separately and are heat sealed together at 41; however, the two portions might be integrally formed if such a construction were desired. It will be observed that flange portion 40 extends a substantial distance radially outwardly beyond the two coupling rings 16, 37, and is provided with a bead 40a about the outer perimeter thereof. In a relaxed or untensioned state, the annular flange portion 40 preferably has a gentle forward curvature (when viewed in radial section as in FIG. 2) so that its rear surface 40b—the surface facing faceplate 30—has a slight convex curvature.

The particular coupling ring assembly depicted in the drawings utilizes a double-ribbed channel construction and a spring member 39 that cooperates with both ribs within the channel to produce a highly effective sealing interlock between the parts. For a more complete disclosure of such assembly, reference may be had to copending co-owned application Ser. No. 358,639, filed Mar. 16, 1982. It is to be understood that the floating feature disclosed in the present application may be used with other types of coupling ring assemblies such as, for example, the prior ring assemblies revealed by the aforementioned patents, although in such cases the particular advantages to be derived from utilizing the ring assembly of the co-pending application would not be realized.

A thin annular web 42 of flexible and resilient thermoplastic material joins the periphery of flange portion 40 to faceplate 30. Specifically, the outer edge portion 42a of the thermoplastic web is heat sealed at 43 to the periphery of flange portion 40, and the inner edge portion 42b, which defines an opening 44 of smaller diameter than opening 45 of ring 37, is joined by heat seal 46 to the faceplate 30. In the embodiment illustrated, the faceplate 30 includes an annular mounting collar 30a which reinforces the faceplate in the area about opening 44 and heat seal 46. The collar is secured to the remainder of the faceplate by a second heat seal 47, as illustrated in FIG. 2. For a detailed discussion of the mounting collar and faceplate arrangement and its advantages, reference may be had to co-owned U.S. Pat. No. 4,213,358. While web 42 and collar 30a are shown to have their inner edges spaced outwardly beyond the edge of opening 34, the web and collar may be extended closer to opening 34, in which case the heat seal zone 46 would also be enlarged (extended inwardly) to correspond with the increased inward dimensions of the web and collar.

The mounting collar 30a, if used, should be formed from a tough material that may be readily sealed to both the remainder of faceplate 30 and to web 42. Thus, if the remainder of the faceplate 30 is formed of an ethylene vinyl acetate copolymer, then the reinforcing mounting collar 30a may be formed of a material of similar composition, although not necessarily microporous. The rings 16 and 37, including flange portion 40, may be formed from any suitable semi-rigid polymeric material having sufficient toughness and durability to withstand repeated latching and unlatching, as well as being inert to body fluids and being heat sealable to adjoining elements. A polyolefin such as polyethylene has been found particularly effective, but other materials having similar properties may be used. Web 42 must not only be heat sealable, tough, and durable, but should also function as a fluid and odor barrier. Low density polyethylene coextruded with a coextensive layer or core of polyvinylidene chloride, known under the designation Saranex, from Dow Chemical Company, Midland, Michigan, has been found suitable but, again, other materials having similar properties are available and may be used.

It is believed evident from FIGS. 2, 3, and 5 that some resilience of the flexible web 42 is important since, as coupling ring 37 is moved axially away from faceplate 30, the web would ordinarily be subjected to stretching forces and, conversely, when the coupling ring 37 is returned to its original position of FIG. 2, such stretching forces would be relieved. The extent of such resilience, or stretchability and recoverability, need only be slight. Specifically, the resilience should not be so low that the ring is brittle and tends to crack or rupture in response to such stretching forces, nor so great that the ring is excessively pliant and allows the pouch assembly to droop, shifting the openings of the respective coupling rings out of general alignment with the opening 44 defined by the inner margin of web 42, when the appliance is in use.

The importance of the limited floating relationship between coupling ring 37 and faceplate 30 is indicated in FIGS. 3–5. The annular web 42 allows a wearer (or a nurse or other attendant to place his/her fingers behind the second coupling rings 37—that is, between the coupling ring and faceplate 30—to brace ring 37 so that it may be coupled to ring 16. The coupling action is carried out simply by squeezing the two rings together in the manner illustrated in FIG. 4. In that view, the wearer's thumb is inserted behind web 42 and coupling ring 37, and other fingers engage wall 13b of the pouch which in turn contacts wall 13a to force the rings together into the fully coupled positions depicted in FIG. 5. The interlocking of the two coupling rings is therefore achieved without urging ring 37 rearwardly and without exerting pressure on the tender peristomal area. Since the limited floating relationship between ring 37 and faceplate 30 allows the user's fingers to directly contact the rear surface of web 42 in bracing the coupling ring 37 during a coupling operation, such contact promotes tactile confirmation that a coupling or latching action has in fact occurred. Such tactile confirmation is particularly effective if the coupling rings are constructed to produce a snap action as they are latched together.

Uncoupling of the rings is achieved by gripping tab 28 and pulling it radially outwardly (to disengage a portion of rib 26 from latching member 39) and then forwardly. During such operation, the wearer (or other person) immobilizes ring 37 by gripping flange 40 in the area adjacent tab 28. Again, such action may be carried out without transmitting any appreciable forces to the faceplate that might cause patient discomfort or result in separation (or weakening) of the adhesive seal between the faceplate and the patient.

The slight convex curvature of the rear surface of flange portion 40, when that portion is in an untensioned or undeformed state as shown in FIG. 2, makes it easier for a user to insert one or more fingers behind the flange in the manner depicted in FIG. 3. The tensioning of web 42 is such that, in an unstretched or untensioned state, the web tends to extend along a plane parallel to faceplate 30, except to the extent that the curvature of the flange portion causes the periphery of the web to be spaced a slight distance from the faceplate. That slight distance is all that is needed to permit a user to slip one or more fingers behind the web for the purposes of bracing ring 37 during a coupling operation or of gripping the periphery of flange portion 40 between the fingers during an uncoupling procedure.

The floating relationship between the flange-equipped coupling 37 and faceplate 30 is important not only during attachment and detachment of the rings but also during wearing of the ostomy appliance. FIG. 5 shows that web 42 allows considerable forward-rearward (axial) movement of the coupled rings independently of any movement of faceplate 30. Conversely, the flexible and deformable faceplate may be easily shaped to follow body contours and to insure an effective seal against the patient without objectionable resistance from the relatively stiff coupling ring 37 and its flange portion 40. Compliance by the faceplate is therefore achieved without constraints that might reduce the effectiveness of the adhesive seal and without subjecting ring 37 to deforming forces that might result in unintentional uncoupling of the two rings, and the relatively stiff coupling rings are allowed to remain in coplanar sealing relationship despite the curvatures formed in the faceplate and the constant flexing that such faceplate undergoes during movement of the wearer's body.

While in the foregoing an embodiment of the invention has been disclosed in considerable detail for purposes of illustration, it will be understood by those skilled in the art that many of these details may be varied without departing from the spirit and scope of the invention.

I claim:

1. An ostomy appliance comprising a flexible collection pouch and a flexible, apertured faceplate adapted to be adhesively secured to a peristomal surface, and a pair of first and second semi-rigid coupling rings detachably connectable to each other, said first coupling ring being secured to said pouch and communicating with the interior thereof, and said second coupling ring being mounted upon said faceplate adjacent the aperture thereof, wherein the improvement comprises said second ring being mounted upon said faceplate by flexible annular plastic web means having a pair of concentric edge portions, one of said edge portions being connected to said second ring and the other of said edge portions being connected to said faceplate about the aperture thereof, said flexible web means allowing limited movement of said second ring in generally axial directions normal to said faceplate to permit insertion of the fingers between said second ring and said faceplate and thereby facilitate attachment and detachment of said rings without causing wearer discomfort and to allow conformity of said flexible faceplate to a wearer's body without objectionable resistance from said semi-rigid rings.

2. The appliance of claim 1 in which said web, means when in an untensioned state, lies along a plane generally parallel with a plane normal to the centerline axis of said second coupling ring.

3. The appliance of claims 1 or 2 in which said second ring includes a radially and circumferentially extending annular flange portion, said one edge portion of said web means being secured to said flange portion adjacent the perimeter thereof.

4. The appliance of claim 3 in which said flange portion is provided with a bead along the perimeter thereof.

5. The appliance of claim 4 in which said annular flange portion has a slight convex curvature along the surface thereof facing towards said faceplate.

6. The appliance of claims 1 or 2 in which said flexible web means is formed from a resilient thermoplastic material.

7. The appliance of claim 1 in which said second ring is formed of polyolefin.

8. The appliance of claim 7 in which said polyolefin is polyethylene.

9. An ostomy appliance comprising a flexible collection pouch and a flexible, apertured faceplate adapted to be adhesively secured to a peristomal body surface, and a pair of first and second semi-rigid coupling rings detachably connectable to each other, said first coupling ring being secured to said pouch and communicating with the interior thereof, sand said second coupling ring being mounted upon said faceplate about said aperture, wherein the improvement comprises said second ring being mounted upon said faceplate by thin, resilient, thermoplastic annular web means having inner and outer concentric edge portions, said second ring also including a radially and circumferentially extending annular flange portion projecting outwardly beyond said first ring when said coupling rings are connected to each other, said outer edge portion of said web means being secured to said flange portion adjacent the outer periphery thereof and said inner edge portion of said web means being secured to said faceplate about and adjacent to said aperture, said flexible web means allowing limited movement of said second ring in generally axial directions normal to said faceplate to permit insertion of the fingers between said second ring and said faceplate and thereby facilitate attachment and detachment of said rings without causing wearer discomfort and to allow conformity of said flexible faceplate to a wearer's body without objectionable resistance from said semi-rigid rings.

10. The appliance of claim 9 in which said web means, when in an untensioned state, lies along a plane generally parallel with a plane normal to the axis of said second coupling ring.

11. The appliance of claim 9 in which said flange is provided with a bead extending along the outer perimeter thereof.

12. The appliance of claim 11 in which said annular flange portion has a slight convex curvature along the surface thereof facing towards said faceplate.

13. A faceplate and coupling ring assembly for an ostomy appliance, comprising a flexible apertured faceplate adapted to be adhesively secured to a peristomal body surface, a relatively rigid coupling ring joined to said faceplate by flexible, resilient, annular plastic web means having inner and outer edge portions, said outer edge portion being secured to said ring and said inner edge portion being secured to said faceplate about the aperture thereof, said web means, when in an untensioned state, lying along a plane generally parallel with the plane of said coupling ring, said coupling ring being adapted for detachably engaging a mating coupling ring mounted upon a collection pouch, said flexible web means allowing limited movement of the first-mentioned coupling ring in generally axial directions normal to said faceplate to permit insertion of the fingers between said first-mentioned ring and said faceplate and thereby facilitate attachment and detachment of said first-mentioned coupling ring and said mating coupling ring without causing wearer discomfort and to allow conformity of said flexible faceplate to a wearer's body without objectionable resistance from said coupling rings.

14. The assembly of claim 13 in which said first mentioned coupling ring is concentric with said aperture.

15. The assembly of claim 13 in which said first mentioned coupling ring includes a radially and circumferentially extending annular flange portion, said outer edge portion of said web means being secured to said flange portion adjacent the perimeter thereof.

16. The assembly of claim 15 in which said annular flange portion has a slight convex curvature along the surface thereof facing towards said faceplate.

17. The assembly of claims 15 or 16 in which said flange portion is provided with a bead extending about the perimeter thereof.

* * * * *